United States Patent [19]
Stork et al.

[11] Patent Number: 5,636,326
[45] Date of Patent: Jun. 3, 1997

[54] METHOD FOR OPERATING AN OPTIMAL WEIGHT PRUNING APPARATUS FOR DESIGNING ARTIFICIAL NEURAL NETWORKS

[75] Inventors: David G. Stork; Babak Hassibi, both of Stanford, Calif.

[73] Assignee: Ricoh Corporation, Menlo Park, Calif.

[21] Appl. No.: 499,386

[22] Filed: Jul. 7, 1995

Related U.S. Application Data

[62] Division of Ser. No. 297,702, Aug. 29, 1994, abandoned, which is a continuation of Ser. No. 940,687, Sep. 4, 1992, abandoned.

[51] Int. Cl.$^6$ ................................................. G06F 15/18
[52] U.S. Cl. ........................................ 395/21; 395/23
[58] Field of Search ............................ 395/21, 23, 24

[56] References Cited

U.S. PATENT DOCUMENTS

| | | | |
|---|---|---|---|
| 5,046,020 | 9/1991 | Filkin | 395/23 |
| 5,129,039 | 7/1992 | Hiraiwa | 395/24 |
| 5,228,113 | 7/1993 | Shelton | 395/23 |

OTHER PUBLICATIONS

Chiselli–Crippa et al., "A Fast Neural Net Training Algorithm and its Application to voiced–Unvoiced–Silence Classification of Speech," Int'l. Conf. on Acoustics, Speech, and Signal Processing, pp.441–444.

Yuan et al., "Towards Constructing Optimal Feedforward neural networks with Learning and Generalization Capabilities," Int'l. Forum on Applications of Neural Nets to Power Systems, pp. 227–231.

E.D. Karnin, "A Simple Procedure for Pruning Back–Propagation Trained Neural Networks," IEEE Trans. on Neural Networks, V. 1 (2), pp. 239–242.

Hirose et al., "Back–Propagation Algorithm which Varies the Number of Hidden Units," Neural Networks, V. 4 (1), pp. 61–66.

LeCun et al., "Optimal Brain Damage," Neural Information Processing Systems, V. 2, pp. 598–605.

C. Bishop, "Exact Calculation of the Hessian Matrix for the Multilayer Perceptron," Neural Computation, V. 4 (4), pp. 494–501.

*Primary Examiner*—Robert W. Downs
*Attorney, Agent, or Firm*—Blakely, Sokoloff, Taylor & Zafman

[57] ABSTRACT

A method and apparatus for designing a multilayer feed forward neural network that produces a design having a minimum number of connecting weights is based on a novel iterative procedure for inverting the full Hessian matrix of the neural network. The inversion of the full Hessian matrix results in a practical strategy for pruning weights of a trained neural network. The error caused by pruning is minimized by a correction that is applied to remaining (un-pruned) weights thus reducing the need for retraining. However, retraining may be applied to the network possibly leading to further the simplification of the network design.

12 Claims, 6 Drawing Sheets

METHOD FOR OPERATING AN OPTIMAL WEIGHT PRUNING APPARATUS FOR DESIGNING ARTIFICIAL NEURAL NETWORKS

This is a divisional of application Ser. No. 08/297,702, filed Aug. 29, 1994, now abandoned, which is a continuation of application Ser. No. 07/940,681, filed Sep. 4, 1992, now abandoned.

FIELD OF THE INVENTION

The present invention relates to the manufacture and design of multilayer artificial neural networks and more specifically to the design and manufacture of networks with a reduced number of interconnections resulting in improved generalizing characteristics and minimal increase in training error.

BACKGROUND OF THE INVENTION

Artificial neural networks (ANNs) are typically designed and constructed as a multilayer structure having one or more hidden layers of artificial neurons (ANs) and an output layer of ANs as shown in FIG. 1. Most commonly, each layer consists of a number of ANs and each AN comprises a node and a group of weighted input receptors or synapses. The weighted receptors couple the output of lower level ANs to the nodes of the next higher layer through a weighting element that modifies the amplitude of the input signal to the receptor. The node sums the weighted receptor inputs and applies the sum to a monotonically increasing nonlinear element that produces the output signal of the node. Thus, the number of weighted receptors in any given layer may be equal to the product of the number of ANs (or nodes) and the number of nodes in the next lower layer. The total number of weighting elements may be as large as $KN^2$, where K is the number of layers and N is the average number of nodes per layer. A modest ANN that accommodates an input vector with 100 component signals could have as many as 10,000 weighting elements per layer. This would not be an excessively large network compared to networks reported to have $6.5 \times 10^6$ weights with 2600 input parameters. A central problem in the design of neural networks is minimizing the complexity of the network so that the resulting ANN complexity is consistent with the training data available. Complexity management translates into minimizing the number of weights. It is well-known that without such network "pruning" a mismatch between the number weights used in the network and the "degrees of freedom" (complexity) will result in sub-optimal performance. Having too many weights (high complexity) leads to overfitting and hence poor generalization. Conversely, if too few weights are used (insufficient complexity), the network's ability to learn will be impaired. Generalization is optimized by trading off network complexity and training error. Unfortunately, no simple method for determining the required degree of complexity, prior to a trial training session, is available.

Consequently, even when an ANN is trained and found to function adequately on the available training data, it is not apparent that the complexity of the ANN is commensurate with the objective. Elimination of weights and/or ANs and retraining suggests itself. However, it is not clear how such pruning is to be done. In other words an efficient rational pruning method is needed as a guide to reducing the complexity of a trained ANN.

Hertz et al. have proposed a pruning method based on removing weights having the smallest magnitude (Hertz, J. Krogh, A., and Palmer, R. G. "Introduction to the theory of Neural Computation," Addison Wesley 1991). This idea unfortunately often leads to the elimination of the wrong weights in high order ANNs because the combined affect of low magnitude weights may be essential for low error.

A method for reducing ANN size by selectively deleting weights that is applicable to large scale networks has been described by LeCun et al. (LeCun, Y., Decker, J. S., and Solla, S. A., (1990) "Optimal Brain Damage", Neural Information Processing Systems, Vol. 2, Touretzky, D. S. (ed.) pp. 598–605, Morgan-Kaufmann). The method is based on a theoretical measure using the second derivative of the objective function with respect to the weighting parameters for computing the saliencies. Saliency is defined to be the change in objective function caused by deleting that parameter. Because it is prohibitively laborious to evaluate the saliency directly by deleting each parameter and evaluating the objective function, an analytical prediction of saliency is used based on a Taylor series expansion of the objective error function. A perturbation of the weight vector w by δw causes a perturbation in value of the error objective function or metric, E, corresponding to E+δE where $$\partial E = \frac{1}{2} \sum_{i=1}^{N} \sum_{j=1}^{N} h_{ij} \delta w_i \delta w_j \quad (1)$$

$$h_{ij} = \partial^2 E / \partial w_i \partial w_j$$

and $\delta w_k$, an element of δw, the perturbation introduced into the weight $w_k$ of vector w.

By assuming that only the diagonal terms (i=j) are significant, LeCun et al. arrive at the simplified saliency measure $$\delta E = \frac{1}{2} \sum_{i=1}^{N} h_{ij} \delta w_i^2 \quad (2)$$

Thus, by analytically determining the values of $h_{ij} = \partial E/\partial^2 w_i$, the effect of any change in weights, $\delta w_i$, on the objective, δE, may be estimated from the known activation function characteristics of the ANs used, and from the topology of the ANN.

The simplifying assumption made by LeCun et al. may lead to sub-optimal results if the off-diagonal terms ($h_{i,j}$; j|i) are significant.

Another approach requires that statistical tests be performed on weights during training. If a weight is not "statistically significant from zero," then that weight is to be eliminated or reduced in value (decayed) (Hertz et al., op. cit.). Unfortunately, the statistical tests are performed during training, and it is unclear how the statistics of the weight during training relates to the final trained network.

For example, a set of benchmark problems were used in a recent competition in machine learning (Thrun, S. B., and 23 co-authors (1991), "The MONK's Problems—A Performance Comparison of Different Learning Algorithms", CMU-CS-91-197 Carnegie-Mellon Univ. Dept. of Comp. Science Tech, Repo.), the most successful method was back propagation using weight decay, which yielded a network with 58 weights for one MONK's problem. The method of the present invention requires only 14 weights for the same performance and on two other MONK's problems, resulted in a 62% and 90% reduction in the number of weights.

SUMMARY AND OBJECTS OF THE INVENTION

One of the objects of the present invention is to an optimal manufacturing and design method for pruning neural network weights based on a Taylor series expansion of the predicted error.

Another object is to provide a pruning method that does not require any restrictive assumptions on the network's Hessian matrix.

Another object is to provide a method for pruning and adjusting the remaining weights so that retraining is not required.

Another object is to provide a pruning method that results in a minimal increase in error and may result in an overall reduction in error.

Another object is to provide a neural network structure with a minimal set of weights based on use of the Hessian matrix.

Another object is to provide a manufacturing and design apparatus for manufacturing minimum complexity networks.

A method and apparatus for the design and manufacture of optimal neural networks featuring a minimum number of weights is based on the inversion of the full Hessian matrix of the multilayer neural network. The Hessian, which represents all of the second derivative information of the neural network, is inverted by a novel interactive method that makes it practical to invert Hessians of large dimensions. Pruning is based on the selection of minimum saliency candidate elements for elimination combined with a weight correction vector for adjusting the remaining weights without requiring retraining. A total optimally pruned neural network design and manufacture system uses a gradient training system operating cooperatively with an optimal pruning system.

BRIEF DESCRIPTION OF THE DRAWINGS

The present invention is illustrated by way of example and not limitation in the figures of the accompanying drawings, in which like references indicate similar elements and in which:

FIGS. 7(a) and 7(b), shows the improvement in neural network design achieved by the current invention.

DETAILED DESCRIPTION

A method for pruning and adjusting the weights of a feed-forward ANN is described that is based upon a Taylor expansion of the saliency function of the network. The method is suitable as an automated design and manufacturing system when used in conjunction with standard learning methods (such as backpropagation). It is more effective than prior art methods because it takes into consideration the interrelationships among all weights throughout the network. This consideration is important because, from FIG. 1, it is clear that the input to any artificial neuron may be effected by any or all of the weights of lower hidden layers.

Figure 2:
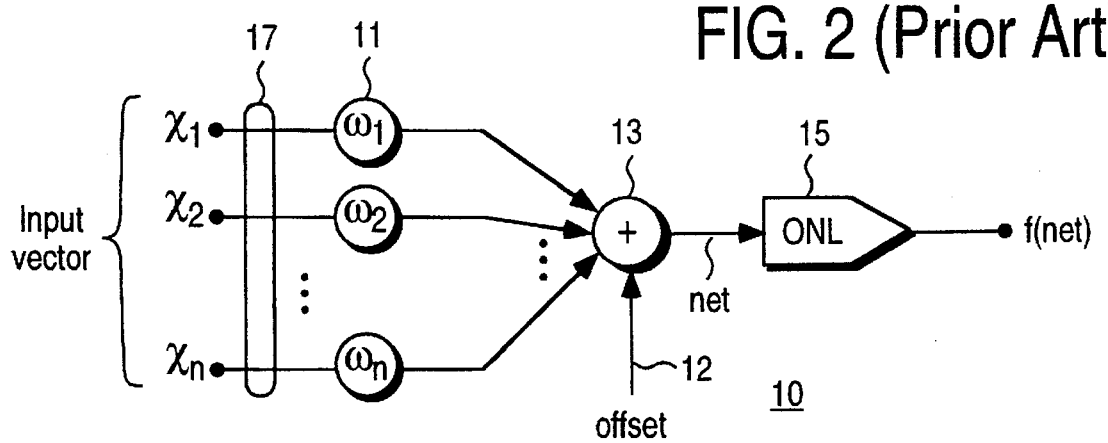
FIG. 2 shows a typical M-P type artificial neural cell.

FIG. 2 provides additional details of the commonly used individual artificial neurons of the M-P (McCullough-Pitts) type. Input data is provided on lines 17 and scaled by the synaptic weights 11 (an offset signal may also be supplied on line 12), summed by summing unit 13 producing the signal "net" which is applied to the sigmoidal output nonlinearity 15 producing output signal f(net).

Because the effects of weight changes will, in general, be coupled to other weight changes, it is reasonable to expect that any pruning strategy should account for the interactive effects.

In the supervised learning mode, a neural network is trained by applying a series of input data vectors to the input terminals of a network with some initial set of weights, represented by the vector, w. The output vector response of the network is then compared to a set of exemplar vector responses that correspond to the desired network response for each input vector. The error metric, E, based on the difference between the desired response and the observed response, is then used to adjust the individual weights of the weight vector, w. Typically, a gradient descent form of algorithm is used such as the well known generalized delta rule or backpropagation rule [Rumelhart, D. E., Hinton, G. E., and Williams, R. J., Learning Internal Representations by Error propagation, Chapt. 8, parallel Distributed Processing, Vol. 1, 1986, Cambridge, MIT Press].

After applying a sufficient set of exemplar input and output vectors, the error reaches an apparent minimum or saddle point in the error as defined by the weight parameter space. The gradient of the error with respect to the weight vector, $\Delta E$, is zero (approximately)

$$\nabla E = \frac{\partial E}{\partial w} = \left[ \frac{\partial E}{\partial w_1} \quad \frac{\partial E}{\partial w_2} \cdots \frac{\partial E}{\partial w_N} \right]^T = 0 \quad (3)$$

and $$w = [w_1 w_2 \ldots w_N]^T$$

where the superscript T denotes the vector transpose.

Although the gradient of the error, $\Delta E$, is zero, the error metric, E, most probably will not be zero.

It is desired to find the saliency or sensitivity of the error metric, E, to perturbations in the component weights of the weight vector, w. This may be obtained by means of a Taylor series expansion of the perturbed error metric as follows:

$$\delta E = \left[ \frac{\partial E}{\partial w} \right]^T \cdot \delta w + \frac{1}{2} \delta w^T \cdot H \cdot \delta w + O(\|\delta w\|^3) \quad (4)$$

where $\delta E$ is the change in the error metric due to changes or perturbations in the weight vector, $\delta w$, $H = \partial^2 E/\partial w^2$ is the Hessian matrix containing all second order derivative information.

$$\delta w = [\delta w_1 \delta w_2 \ldots \delta w_N]^T \quad (5)$$

Because the network is trained to an error minimum, the first term of equation (4), is the gradient, $\Delta E$, which is zero. Also, because the perturbations are assumed to be small, the last term and all higher order terms are also assumed to be zero, resulting in the following approximation relating weight perturbations to error perturbations.

$$\delta E = \frac{1}{2} \delta w^T \cdot H \cdot \delta w \quad (6)$$

where $$H = \begin{bmatrix} H_{11} H_{12} & \cdots & H_{1N} \\ H_{21} H_{22} & \cdots & H_{2N} \\ \cdot & & \cdot \\ \cdot & & \cdot \\ \cdot & & \cdot \\ H_{N1} H_{N2} & \cdots & H_{NN} \end{bmatrix} \quad (7)$$

and $$H_{ij} = \partial^2 E / \partial w_i \partial w_j \quad (8)$$

Thus, if each of term, $H_{ij}$, is evaluated, the effect of a weight vector perturbation, $\delta w$, can be predicted by equation (6).

Because our purpose is to prune or eliminate weights, and upon eliminating a weight to find the necessary adjustment to the remaining weights that minimizes the resulting error, suppose we eliminate weight, $w_q$. This may be algebraically expressed as $$\delta w_q = -w_q \quad (9)$$

or $$\delta w_q + w_q = 0 \quad (10)$$

where $\delta w_q$ and $w_q$ are vector components. If $e_q$ represents the unit vector in weight space corresponding to $w_q$, then the vector dot product of $e_q$ with the vector $\delta w$ yields $$e_q^T \delta w = -w_q$$

or $$e_q^T \cdot \delta w + w_q = 0 \quad (11)$$

In order to minimize $\delta E$ by eliminating the minimum weight, $w_q$, we form a Lagrangian from equations (6) and (11)

$$L = \tfrac{1}{2} \delta w^T \cdot H \cdot \delta w + \lambda (e_q^T \cdot \delta w + w_q) \quad (12)$$

where $\lambda$ is the Lagrangian undetermined multiplier. The Lagrangian, L, represents the increase in error due to eliminating $w_q$.

Equation (12) has two unknowns: $\lambda$, and $\delta w$, which is the change in the weight vector $w$ that is required to minimize the error increase, L, due to eliminating $w_q$. The solution is obtained from equation (12) by taking the functional derivative of L and setting it to zero.

$$\frac{\partial L}{\partial \delta w} = H \cdot \delta w + \lambda e_q = 0 \quad (13)$$

By means of the constraints of equation (11) and the use of matrix inversion to find the Lagrangian multiplier, we obtain $$\lambda = -w_q / [H^{-1}]_{qq} \quad (14)$$

where $[H^{-1}]_{qq} = e_q^T H^{-1} e_q$ which is the $qq^{th}$ component of the inverse of matrix H. The optimal weight change and resulting error change are:

$$\delta w = -(w_q / [H^{-1}]_{qq}) H^{-1} \cdot e_q \quad (15)$$

$$L_q = \tfrac{1}{2} w_q^2 / [H^{-1}]_{qq} \quad (16)$$

Equations (16) and (15) are the desired expressions for $L_q$, the minimum increase in error, due to setting $w_q = 0$, and for adjusting the weight vector, $w$, by the error adjustment vector, $\delta w$.

It is important to note that the new weight vector, $w + \delta w$, is obtained without retraining of the network by the application of training data vectors and suggests three pruning strategies:

(1) Use $w + \delta w$ as the new weight vector;

(2) Use $w + \delta w$ as the new weight vector, retrain the network and optionally re-prune the retrained network as outlined above.

(3) Use $w + \delta w$ as the new weight vector and repeat the pruning process outlined above until the accumulated error increase obtained by successive evaluations of equation (16) exceeds the allowable error budget and then retrain the network.

Because the resulting error function may not be at an exact minimum (due to higher order terms being ignored) retraining may be useful in establishing a better minimum.

It should also be noted that neither H nor $H^{-1}$ need to be diagonal because no simplifying assumption has been made in order that the inverse, $H^{-1}$, be readily obtained from H.

Figure 3:
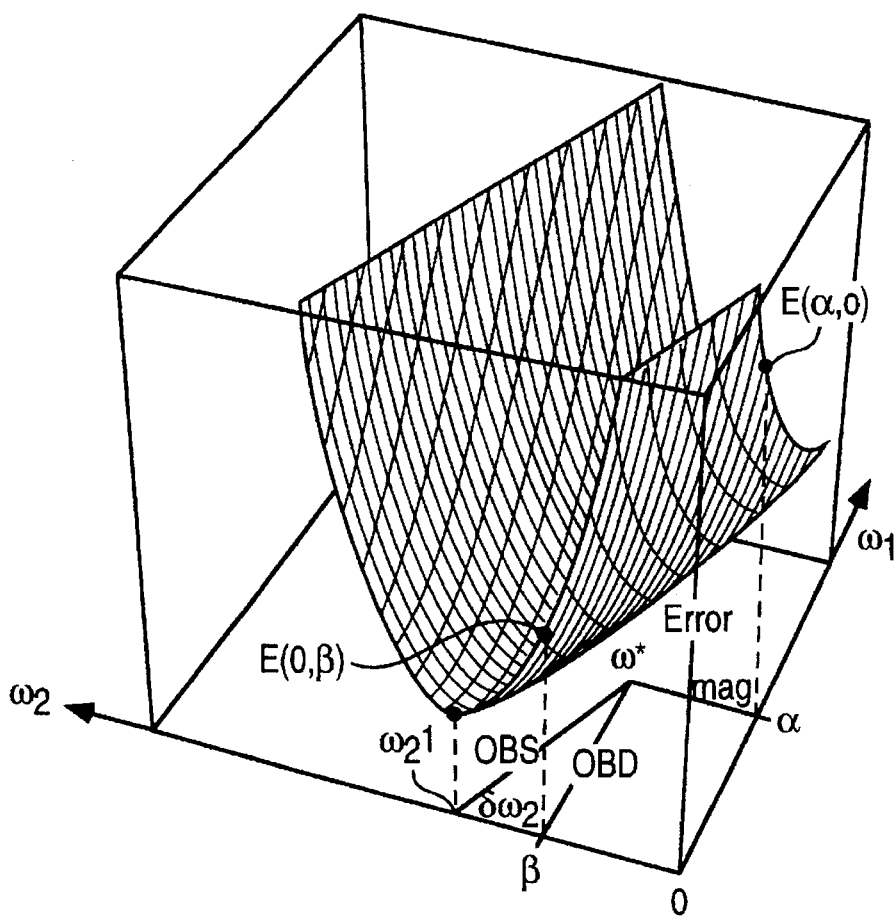
FIG. 3 illustrates an error surface and the affects of various pruning methods on residual error.

For purposes of explanation, FIG. 3 depicts an error surface for a two weight system, $w = [w_1 \ w_2]^T$. The error surface portrayed is general in that it has different curvatures (second derivative) along different directions and a principle axes that is not parallel to either weight axes (which implies a non-diagonal Hessian matrix).

It is assumed that a local minimum has been found by training, perhaps by one of the well known gradient descent methods. The minimum in the error surface is located at $w_1 = \alpha$, $w_2 = \beta$, where $\alpha > \beta$, as shown in FIG. 3. If the smaller weight, $w_2 = \beta$, were to be pruned, the operating point $(\alpha, \beta)$ would move to $(\alpha, 0)$ as shown and the resulting error would increase corresponding to $E(\alpha, 0)$ which lies on the intersection of the error surface and the plane defined by the $w_1$ and Error axes, directly above $w_1 = \alpha$. This procedure corresponds to magnitude based pruning.

If the pruning procedure is based on the simplifying assumption of LeCun et al., the change in weight would be made along a line parallel to the $w_1$, or the $w_2$ axis. In the example shown in FIG. 3, $$L_1 \equiv \frac{1}{2} w_1^2 \frac{\partial^2 E}{\partial w_1^2} < L_2 \equiv \frac{1}{2} w_2^2 \frac{\partial^2 E}{\partial w_2^2} \ .$$

As a result, $w_1$ would be pruned because the error sensitivity (saliency), $L_1$, is less than $L_2$. The resulting error, $E(0, \beta)$, would lie in the $w_2$, E plane. For this example, the error would be less than obtained by use of weight magnitude information only.

If the optimal weight pruning method of this invention is used, the weight $w_1$ would be pruned as per LeCun et al., because it would be the least saliency defined in this invention (Eq. 16). However, because the Hessian matrix, H, was not assumed to be diagonal, equation (15) provides a correction to the value of $w_2$ so that the minimum error lies at $(0, w_2')$ where $$w_2' = w_2 + \delta w_2 \quad (17)$$

Noting that, for the example of FIG. 3, $$\delta w = [\delta w_1 \delta w_2]^T \quad (18)$$

$$w_q = w_1 \quad (19)$$

so that $$e_q = e_1 = [1 \ 0]^T \quad (20)$$

and letting $$H^{-1} = \begin{bmatrix} G_{11} G_{12} \\ G_{21} G_{22} \end{bmatrix} \quad (21)$$

substitution of the above in equation (15) obtains $$\begin{bmatrix} \delta w_1 \\ \delta w_2 \end{bmatrix} = \frac{-w_1}{G_{11}} \begin{bmatrix} G_{11} G_{12} \\ G_{21} G_{22} \end{bmatrix} \begin{bmatrix} 1 \\ 0 \end{bmatrix} \quad (22)$$

so that $$\delta w_1 = -w_1 \quad (23)$$

$$\delta w_2 = -\left(\frac{G_{21}}{G_{11}}\right) w_1 \quad (24)$$

Thus, equation (23) restates the pruning of weight $w_1$, (i.e., $\delta w_1 + w_1 = 0$), while equation (24) gives the correction $\delta w_2$, of equation (17) that must be applied to $w_2$.

Referring back to FIG. 3, this correction is indicated by the shift, $\delta w_2$, from $E(0, w_2)$ to $E(0, w_2')$ by the distance $-(G_{21}/G_{11})w_1$. As a result, the error returns to the trough of the error surface.

In summary, the method described has the following major steps:

(1) Train the network to a minimum error using well established training procedures.

(2) Compute $H^{-1}$ from the known ANN topology, known activating functions (output nonlinearities) and synaptic weights.

(3) Find the "q" that gives the smallest error increase as smaller than the total error, E, the $q^{th}$ weight should be deleted. Otherwise go to step 5.

(4) Use the value of q from step 3 to update all weights by $$\delta w = -(w_q/[H^{-1}]_{qq}) H^{-1} \cdot e_q \quad (15)$$

and return to step 2.

(5) Because no more weights may be deleted without a large increase in E, the process ends or the the overall cycle can be repeated by retraining the network (going to step 1).

Figure 5:
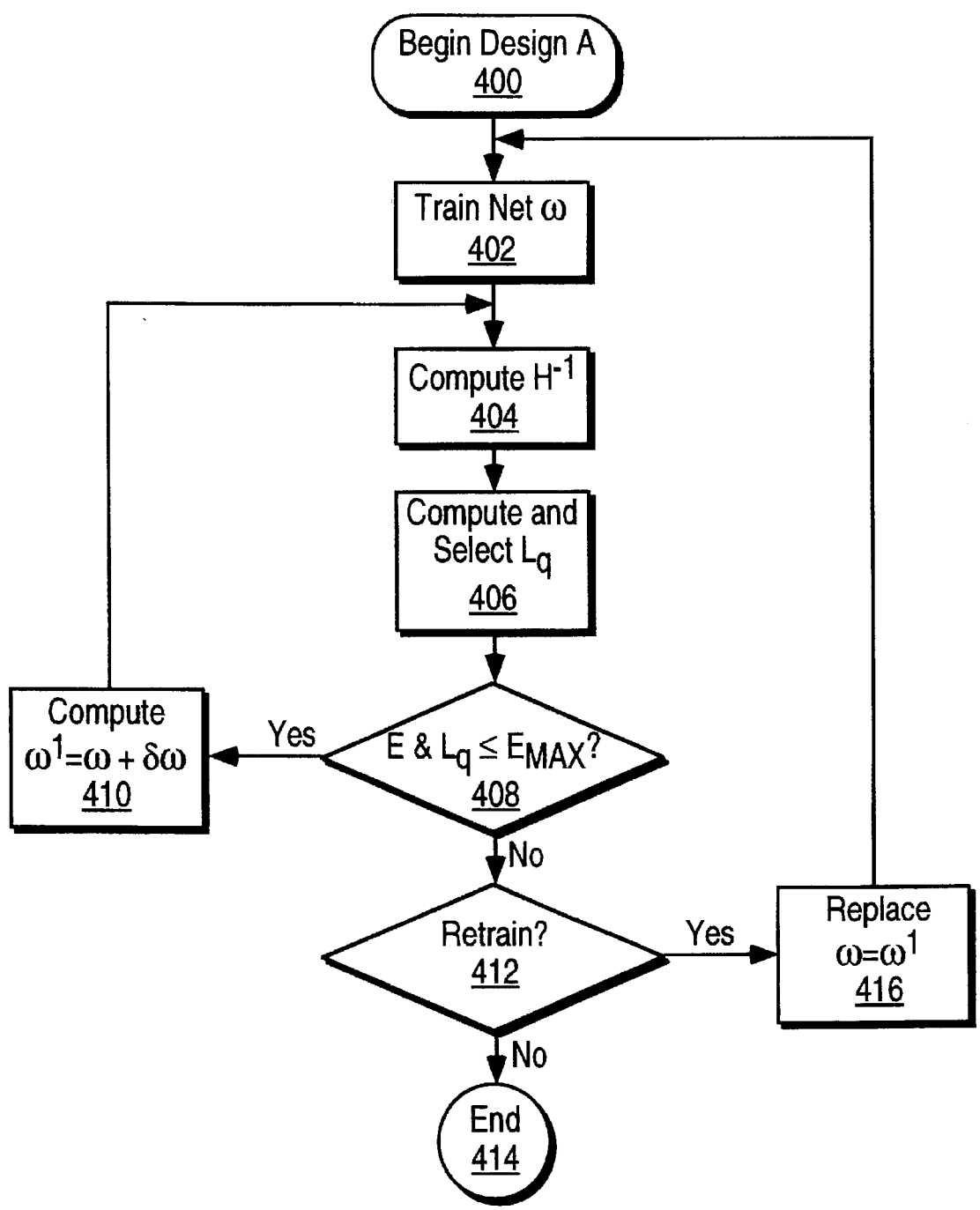
FIG. 5 is a flow diagram for the optimum pruning design method.

FIG. 5 is a flow diagram of the design procedure "A," beginning at step 400, in accordance with the above description. In step 402 the neural network is trained in accordance with anyone of the known gradient or rule-based rules, yielding a set of weights represented by the weight vector, w. From the topological, neural activation function descriptions, and the vector w, the Hessian inverse is computed in step 404. Step 406 computes the saliences of the weights and finds the weights $w_q$ with the smallest saliency, $L_q$. Step 408 tests to see if the resulting error from the pruning of $w_q$, $E+L_q$, is less than the maximum a variable error, $E_{max}$. If not, the required weight vector change, $\delta w$, is calculated and a new weight vector $w' = w + \delta w$ is computed in step 410 and the process returns to step 404 for a new trial cycle of pruning. If the error budget is exceeded by the trial $L_q$ in test step 408, the process proceeds to step 412 where a decision is made whether to retrain. If retraining is desired, step 416 replaces the old vector w with the latest updated vector w' from step 410 and the process returns to step 402. Otherwise, the process ends at step 414.

The Hessian is readily computed from the known topology of the ANN, including the weight values and activation functions of each AN in the network. For example see Bishop, C., "Exact Calculation of the Hessian Matrix for the Multilayer Perceptron", Neural Computation 4, 494–501 (1992).

The difficulty in the above outlined procedure appears to be step 2 because inverting a matrix of hundreds or thousands of terms seems computationally intractable. However, it will be shown below that for backpropagation trainable networks, the Hessian has a structure which permits its inverse to be calculated efficiently and robustly, even for large Hessian matrices.

In order for this procedure to be a practical pruning method, an efficient way to calculate the inverse Hessian matrix, $H^{-1}$, must be found, particularly for the very large ANNs involving thousands of weights. Otherwise, the method becomes computationally intractable.

In the following discussion on an efficient method for computing the inverse Hessian matrix, the standard terminology from backpropagation [Rumelhart et al. op. cit.] will be used.

Figure 4:
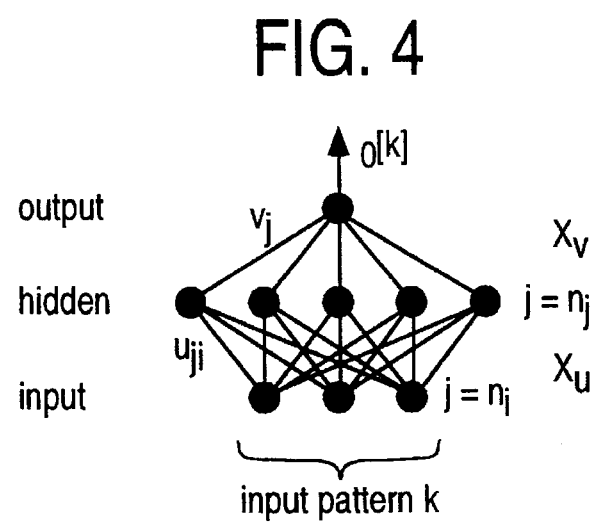
FIG. 4 shows a single output artificial neural network that defines the algebraic indexing.

Consider the ANN of FIG. 4 in which we have an $n_i$ component input vector indexed by $1 < i < n_i$, a set of hidden layer ANs indexed by $1 < j < n_j$, and connected to the input vector by synaptic weights, $u_{ji}$, and an output AN connected to the hidden layer output by synaptic weights $v_j$. (For the sake of clarity, offset inputs to each AN are not shown.) The vectors $X_v$ and $X_u$ refer to second derivative information as described below.

Using the quadratic error function of Rumelhart et al., the error, E, is given by $$E = \frac{1}{2P} \sum_{k=1}^{P} (t^{[k]} - 0^{[k]})^2 \quad (26)$$

where P is the total number of training patterns, [k] is the training pattern index, $t^{[k]}$ is the $k^{th}$ teaching vector exemplar response, and $0^{[k]}$ is the output of the ANN due to the application of the $k^{th}$ input pattern.

The output, $0^{[k]}$, is a function of the input signal, net, supplied to the output activation function $f(\cdot)$, so that $$0^{[k]} = f(net^{[k]})$$

and $$net^{[k]} = \sum_j v_j 0_j^{[k]}$$

where $0_j^{[k]}$ is the $j^{th}$ output of the hidden layer $j^{th}$ neuron and $v_j$ is the associated synaptic weight coupling the $j^{th}$ hidden layer neuron output to the output layer neuron.

Thus, the first partial derivative of equation (26) with respect to the weight $v_j$ is $$\frac{\partial E}{\partial v_j} = -\frac{1}{P} \sum_{k=1}^{P} (t^{[k]} - f(net^{[k]})) \cdot f'(net^{[k]}) \cdot 0_j^{[k]}$$

A second partial differentiation with respect to $v_j$, results in $$\frac{\partial^2 E}{\partial v_j \partial v_j} = \frac{1}{P} \sum_{k=1}^{P} \{f'(net^{[k]})^2 - (t^{[k]} - 0^{[k]})f''(net^{[k]})\} 0_j^{[k]} 0_j^{[k]} \quad (27)$$

In a similar manner, two additional second partial derivatives with respect to output synaptic weights, $\{v_j\}$, and hidden layer synaptic weights, $\{u_j\}$, are obtained from equation (26):

$$\frac{\partial^2 E}{\partial v_j \partial u_{ji}} = \quad (28)$$

$$\frac{1}{P} \sum_{k=1}^{P} \{\{f'(net^{[k]})^2 - (t^{[k]} - 0^{[k]})f''(net^{[k]})\}v_j f'(net_j^{[k]}) 0_i^{[k]} 0_j^{[k]}\} -$$

$$(t^{[k]} - O^{[k]}) f'(net^{[k]}) f'(net_j^{[k]}) \delta_{ij} O_i^{[k]}\}.$$

$$\frac{\partial^2 E}{\partial u_{ji} \partial u_{ji}} = \frac{1}{P} \sum_{k=1}^{P} \{ \{f'(net^{[k]})^2 - (t^{[k]} - \qquad (29)$$

$$O^{[k]}) f''(net^{[k]}) \} v_j v_j f'(net_j^{[k]}) f'(net_{j'}^{[k]}) O_i^{[k]} O_{i'}^{[k]} -$$

$$(t^{[k]} - O^{[k]}) f'(net^{[k]}) v_j f''(net_j^{[k]}) \delta_{ij} O_i^{[k]}\}$$

where $\delta$ is the Kronecker delta and $net_j$ is the input signal to the activation function of the $j^{th}$ hidden layer neuron.

Because these second derivatives need only to be evaluated after training when $t^{[k]} \approx O^{[k]}$, equations (27)–(29) simplify to:

$$\frac{\partial^2 E}{\partial v_j \partial u_j} = \frac{1}{P} \sum_{k=1}^{P} f'(net^{[k]})^2 O_j^{[k]} O_j^{[k]} \qquad (30)$$

$$\frac{\partial^2 E}{\partial v_j \partial u_{ji}} = \frac{1}{P} \sum_{k=1}^{P} f'(net^{[k]})^2 v_j f'(net_j^{[k]}) O_i^{[k]} O_j^{[k]} \qquad (31)$$

$$\frac{\partial^2 E}{\partial u_{ji} \partial u_{ji}} = \frac{1}{P} \sum_{k=1}^{P} f'(net^{[k]})^2 v_j v_j f'(net_j^{[k]}) f'(net_{j'}^{[k]}) O_i^{[k]} O_{i'}^{[k]} \qquad (32)$$

The remarkably elegant structure of equations (30)–(32) permits the calculation of the Hessian and its inverse. To see this, first define vectors containing second derivative information for the weight layers v and u (FIG. 4).

$$[X_v^{[k]}]^T = (f'(net^{[k]}) O_1^{[k]}, \ldots, f'(net^{[k]}) O_{n_j}^{[k]}) \qquad (33)$$

$$[X_u^{[k]}]^T = \qquad (34)$$

$$\left( \begin{array}{c} f'(net^{[k]}) f'(net_1^{[k]}) v_1^{[k]} O_1^{[k]}, \ldots, f'(net^{[k]}) f'(net_1^{[k]}) v_1^{[k]} O_{n_i}^{[k]}, \ldots, \\ f'(net^{[k]}) f'(net_{n_j}^{[k]}) v_{n_j}^{[k]} O_1^{[k]}, \ldots, f'(net^{[k]}) f'(net_{n_j}^{[k]}) v_{n_j}^{[k]} O_{n_i}^{[k]} \end{array} \right)$$

where for $X_u$, lexico-graphical ordering over the input and hidden units is used. These vectors are concatenated to form a full vector of second derivative information throughout the network (evaluated for a single pattern [k]):

$$X^{[k]} = \begin{pmatrix} X_v^{[k]} \\ X_u^{[k]} \end{pmatrix} \qquad (35)$$

The dimensionality of X is equal to the total number of weights in the network. The Hessian, evaluated at a local minimum, is then simply:

$$H = \frac{\partial^2 E}{\partial w^2} = \frac{1}{P} \sum_{k=1}^{P} X^{[k]} \cdot X^{[k]T} \qquad (36)$$

The full Hessian is calculated by sequentially adding in successive "component" Hessians (equation (36)) as:

$$H_{m+1} = H_m + 1/p X^{[m+1]} \cdot X^{[m+1]T} \qquad (37)$$

with $H_0 = \alpha 1$ and $Hp = H$. The solution to equations (14)–(16) requires the inverse of H. This inverse can be calculated using a standard matrix inversion formula (Kailath, T., Linear Systems, Prentice Hall, 1980) as follows:

$$(A + B \cdot C \cdot D)^{-1} = A^{-1} - A^{-1} \cdot B \cdot (C^{-1} + D \cdot A^{-1} \cdot B)^{-1} \cdot D \cdot A^{-1} \qquad (38)$$

which applied to each term in the analogous sequence in equation (37), yields $$H_{m+1}^{-1} = H_m^{-1} - \frac{H_m^{-1} \cdot X^{[m+1]} \cdot X^{[m+1]T} \cdot H_m^{-1}}{P + X^{[m+1]T} \cdot H_m^{-1} \cdot X^{[m+1]}} \qquad (39)$$

with $H_0^{-1} = \alpha^{-1} 1$ and $Hp^{-1} = H^{-1}$, and where $\alpha(10^{-8} \leq \alpha \leq 10^{-4})$ is a constant needed to make $H_0^{-1}$ meaningful, and chosen small in order to penalize large $\delta w$, thereby keeping the second order approximation of Eq. 6 valid. This inventive method is insensitive to $\alpha$ over a large range.

Equation (39) is a pivotal result, which permits the calculation of $H^{-1}$ using a single sequential pass through the training data $1 \leq m \leq p$.

Note that the approximations used for equations (30)–(32) induce several very nice computational properties in equation (39). The first is that because of the approximation $t^{[k]} \approx O^{[k]}$, $H^{-1}$ is being evaluated at the desired error minimum, despite the possibility that the network has not been fully trained to this minimum. Moreover, there are no singularities in the calculation of $H^{-1}$. For large dimensional problems this method is better than first computing the Hessian, and then inverting it through standard matrix inversion techniques. Finally, equation (39) is an $O(n^2)$ calculation for an nxn Hessian matrix that may admit efficient $O(n)$ parallel implementations in VLSI.

The method described above was applied to three of the MONK's problems and the results compared with those of Thrun et al. cited previously. The backpropagation network with weight decay of Thrun et al. outperformed all other network and rule-based approaches on these benchmark problems in that extensive machine learning competition.

The following table summarizes the relative pruning effectiveness of the inventive method described on problems MONK 1, 2, and 3. Rows are identified by the method used, i.e., Thrun for Thrun et al. and HS for the present inventive method.

| Problem | Accuracy % Training | Test | Number of Weights | Pruning Method |
|---|---|---|---|---|
| MONK 1 | 100 | 100 | 58 | THRUN |
|  | 100 | 100 | 14 | HS |
| MONK 2 | 100 | 100 | 39 | THRUN |
|  | 100 | 100 | 15 | HS |
| MONK 3 | 93.4 | 97.2 | 39 | THRUN |
|  | 93.4 | 97.2 | 4 | HS |

For all three MONK problems, the accuracy of the current method was made the same as that of Thrun et al. by limiting the degree of pruning. The two accuracy columns, Training and Test, shows the percentage accuracy using training and test vectors, respectively. The next column clearly shows the number of weights required by each method with the current method requiring 14, 15, and 4 versus 58, 39, and 39 for the method of Thrun et al., a reduction of 76%, 62%, and 90%, respectively.

The algorithm described above and flow diagrammed in FIG. 5 represents the basic method for pruning weights. Other practical improvement can be made including:

(1) deletion of all input weights to any hidden unit whose output is rendered ineffectual by the pruning of all weights connected to its output; and (2) deletion of more than one weight at a time in order to avoid the computation of $H^{-1}$ after each single weight deletion.

The first improvement clearly removes any neuron that is not connected to higher output levels and all associated synaptic weights thereby economizing network resources without any loss in performance.

Figure 6:
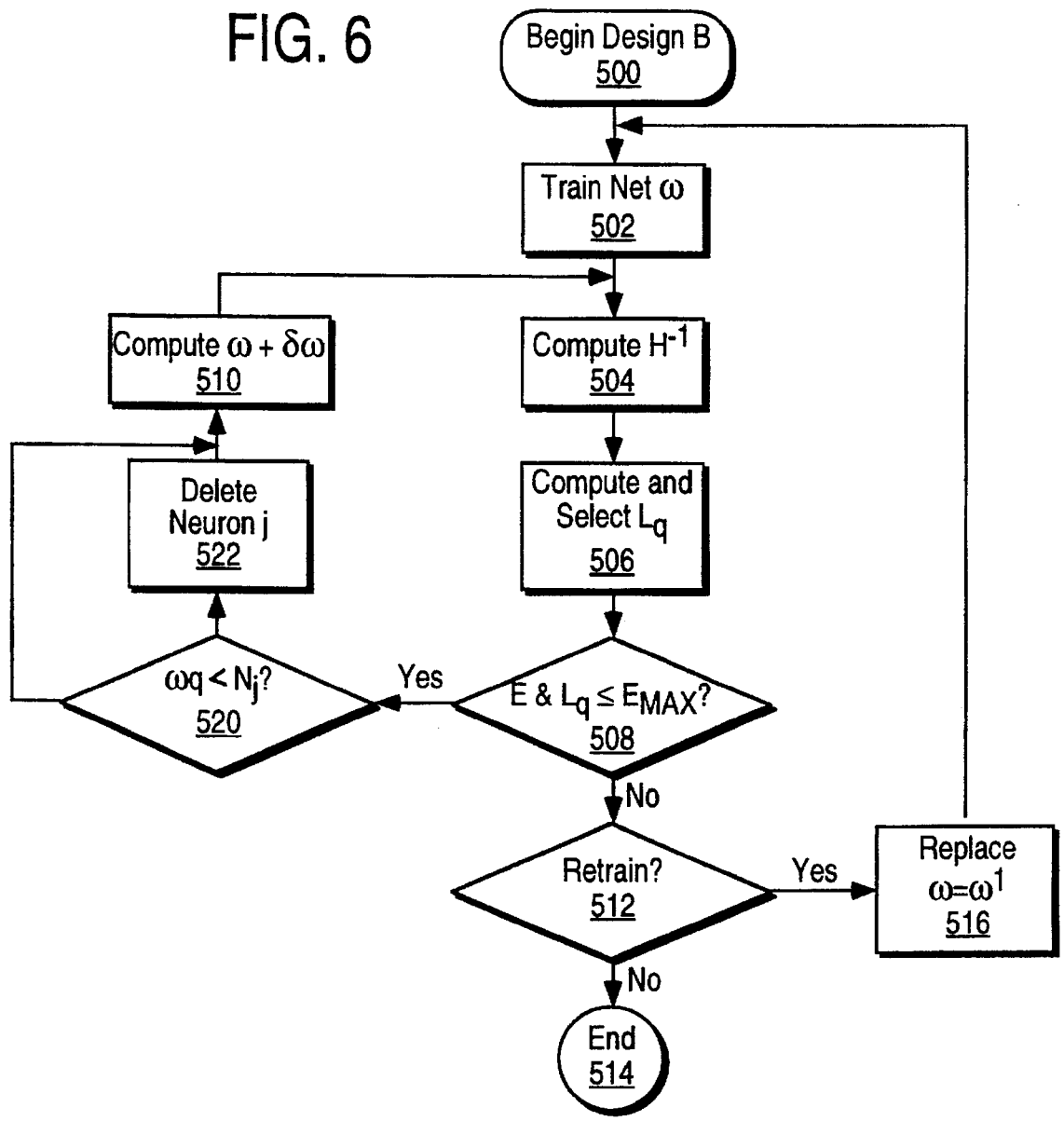
FIG. 6 is a flow diagram of the optimum pruning design method including complete neuron pruning.

FIG. 6 is a flow diagram of the design method "B" in which pruning of entire neurons, including their associated synaptic input weights, whenever a synaptic weight, $v_j$, of the output neuron of a single output network is pruned. The process is identical to that of FIG. 5 except that test step 520 and step 522 have been added. Upon determining that the error budget, $E_{max}$, is not exceeded set 508 by the proposed pruning of $w_q$, step 520 checks if $w_q$ is a synaptic weight of the output layer ($w_q = v_j$) and if so moves to step 522 where neuron j of the hidden layer is deleted, including all of its input synaptic weights. If $w_q$ is not an output synaptic weight, the process moves on to step 510 as in design method "A."

The basis for the second improvement is the following generalizing of equations (15) and (16):

$$\delta w = -H^{-1} \cdot \sum_{j=1}^{m} \lambda_j \theta_j \quad (40)$$

$$\begin{pmatrix} \lambda_{i_1} \\ \cdot \\ \cdot \\ \cdot \\ \lambda_{i_m} \end{pmatrix} = \begin{pmatrix} [H^{-1}]_{i_1 i_1} & \cdots & [H^{-1}]_{i_1 i_m} \\ \cdot & & \cdot \\ \cdot & & \cdot \\ \cdot & & \cdot \\ [H^{-1}]_{i_m i_1} & \cdots & [H^{-1}]_{i_m i_m} \end{pmatrix}^{-1} \begin{pmatrix} w_{i_1} \\ \cdot \\ \cdot \\ \cdot \\ w_{i_m} \end{pmatrix} \quad (41)$$

$$L_q = \frac{1}{2} (w_{i_1}, w_{i_2}, \ldots, w_{i_m}) \cdot \quad (42)$$

$$\begin{pmatrix} [H^{-1}]_{i_1 i_1} & \cdots & [H^{-1}]_{i_1 i_m} \\ \cdot & & \cdot \\ \cdot & & \cdot \\ \cdot & & \cdot \\ [H^{-1}]_{i_m i_1} & \cdots & [H^{-1}]_{i_m i_m} \end{pmatrix}^{-1} \begin{pmatrix} w_{i_1} \\ w_{i_2} \\ \cdot \\ \cdot \\ \cdot \\ w_{i_m} \end{pmatrix}$$

where $w_{i_1} \ldots w_{i_n}$ are the weights corresponding to the lowest set of m saliencies, and $e_{i_1} \ldots e_{i_m}$ are the corresponding unit vector elements.

In general, it may not be practical to find the smallest total saliency, L, of equation (42) over all possible combinations of $i_1$ to $i_m$. However, equation (42) can be used, for the deletion of a whole hidden unit. In this case, $w_q = [w_{q1} \; w_{q2} \; \ldots \; w_{qm}]^T$ would represent the synaptic weights connected to the hidden unit, and $L_q$ would represent the smallest error increase over all hidden units.

A simple heuristic which seems to work, especially for the earliest pruning procedures is to choose $i_1 \ldots i_m$ based on the "single" saliencies computed by equation (16). Although this is not a rigorously valid procedure because deleting a weight would, in general, change the saliencies at the remaining weights. However, it is plausible that such saliency covariance is negligible for large networks.

Figure 1:
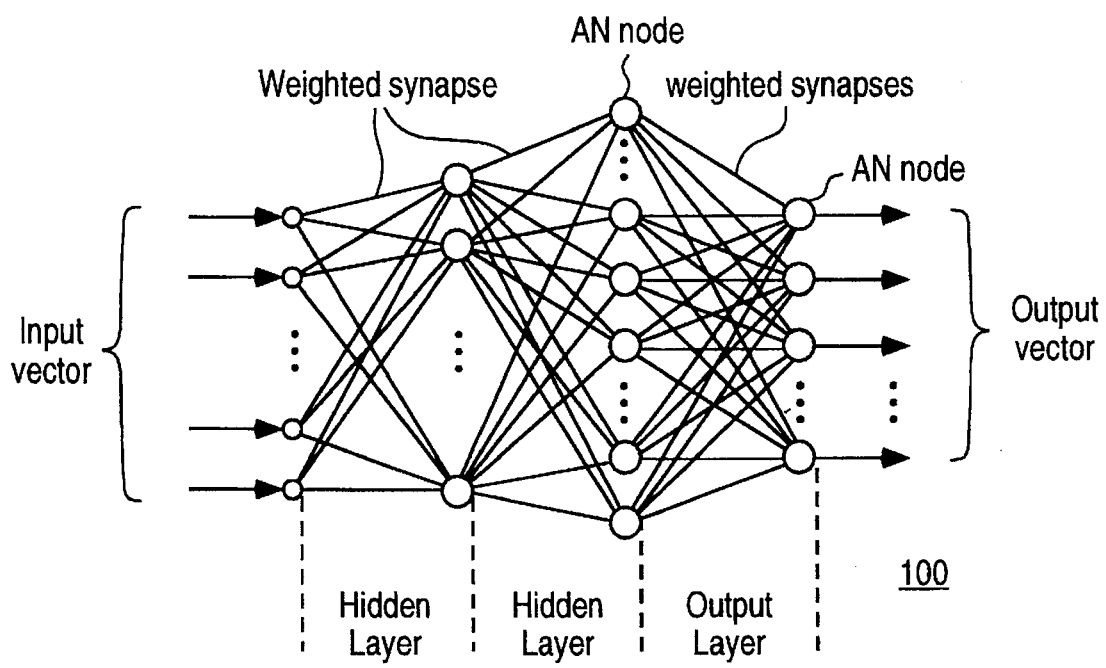
FIG. 1 shows the topology of a multilayer artificial neural network.

Although the pruning design procedure described above has been restricted to a single output node, it is straight forward to generalize to a network with multiple output units. The new expression for the error (analogous to equation (26)) becomes $$E = \frac{1}{2P} \sum_{k=1}^{P} \sum_{b=1}^{n_0} (t^{[bk]} - O^{[bk]})^2 \quad (43)$$

where [bk] is the training index for the $b^{th}$ output node and the $k^{th}$ training pattern, and the second summation is over no output nodes as shown in FIG. 1.

As a result, the Hessian can be written as $$H = \frac{\partial^2 E}{\partial w^2} = \frac{1}{P} \sum_{k=1}^{P} \sum_{b=1}^{n_0} X^{[bk]} \cdot X^{[bk]T} \quad (44)$$

where $$X^{[bk]} = (X_{v_1}^{[1k]T} \delta_{b1}, X_{v_1}^{[2k]T} \delta_{b2}, \ldots, X_{v_m}^{[n_0 k]T} \delta_{b n_0}, X_u^{[bk]T})$$

This leads to the recursion relation for the Hessian:

$$H_{b+1,k} = H_{b,k} + 1/P X^{[b+1\;k]} \cdot X^{[b+1\;k]T} H_{1,k+1} = H_{n_0,k} + 1/P X^{[1\;k+1]} \cdot X^{[1\;k+1]T} \quad (45)$$

which is analogous to equation (37) except that there is a double index on H now, and that $H = H_{n_0 P}$.

The inverse Hessian, $H^{-1}$, obtained as previously described, becomes:

$$H_{b+1,k}^{-1} = H_{b,k}^{-1} - \frac{H_{b,k}^{-1} \cdot X^{[b+1\;k]} \cdot X^{[b+1\;k]T} \cdot H_{b,k}^{-1}}{P + X^{[b+1\;k]T} \cdot H_{b,k}^{-1} \cdot X^{[b+1\;k]}} \quad (46)$$

$$H_{1,k+1}^{-1} = H_{n_0,k}^{-1} - \frac{H_{n_0,k}^{-1} \cdot X^{[1\;k+1]} \cdot X^{[1\;k+1]T} \cdot H_{n_0,k}^{-1}}{P + X^{[1\;k+1]T} \cdot H_{n_0,k}^{-1} \cdot X^{[1\;k+1]}}$$

which again is an iterative solution to the inverse problem that is analogous to equation (39).

Consequently, the design method has the same flow diagram as shown in FIG. 5. Also, FIG. 6 applies if step 520 is interpreted as a test to determine if a subset of the weights, $\{w_q\}$, corresponds to the total set of output cells synaptic weights, $\{v_j\}$, fed by the $j^{th}$ hidden neuron.

Figure 7:
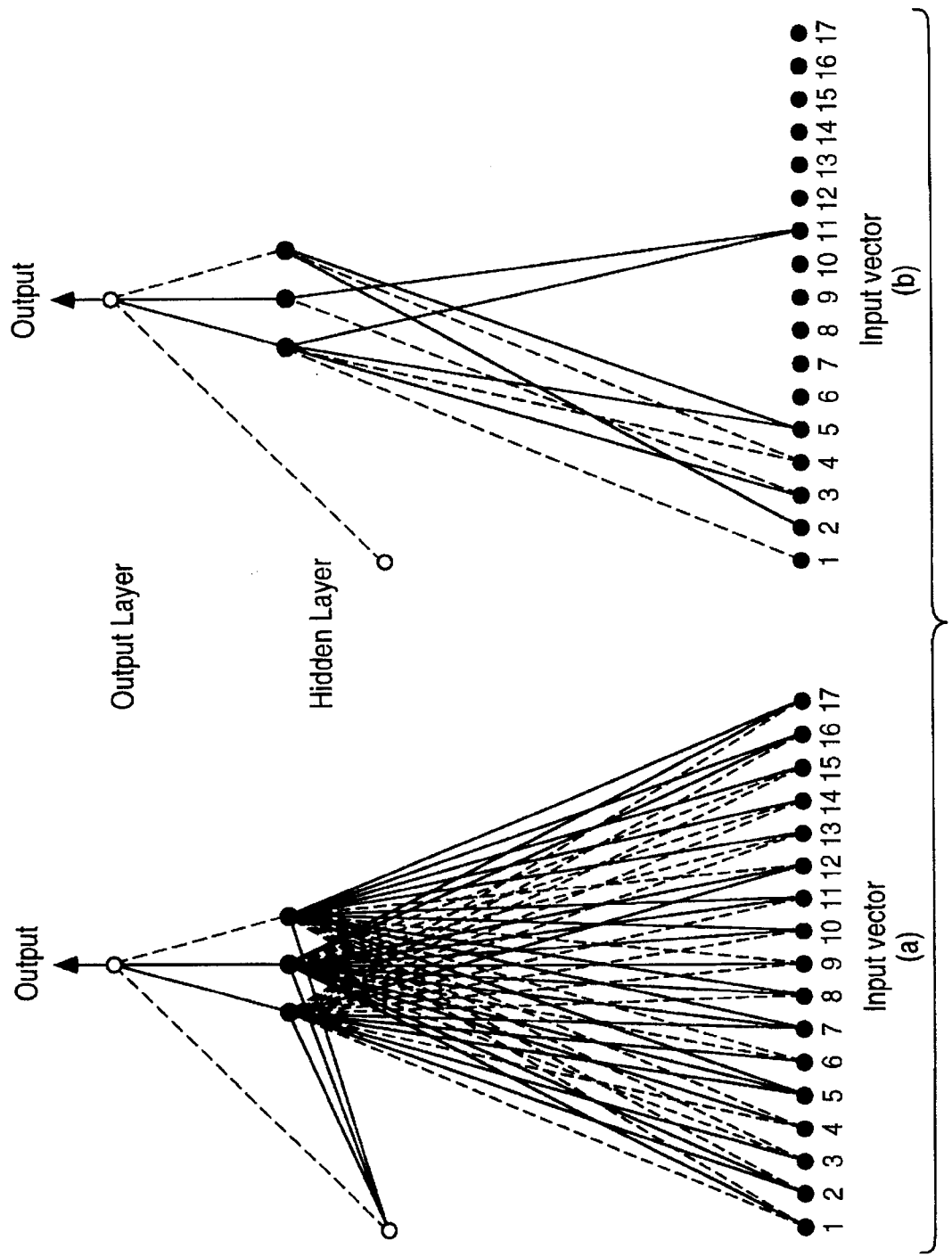
FIG. 7, showing

FIG. 7 graphically demonstrates the improvement in neural network design achieved by the current invention for the MONK 1 problems previously discussed. The solid lines correspond to excitatory weights while the dotted lines correspond to inhibitory weights. The node to the left of the hidden layer of each neural net of FIG. 7 is an offset input. FIG. 7(a) shows the network topology using the Thrun et al. pruning method while FIG. 7(b) is the result of pruning by the present inventive method for equal accuracy.

Figure 8:
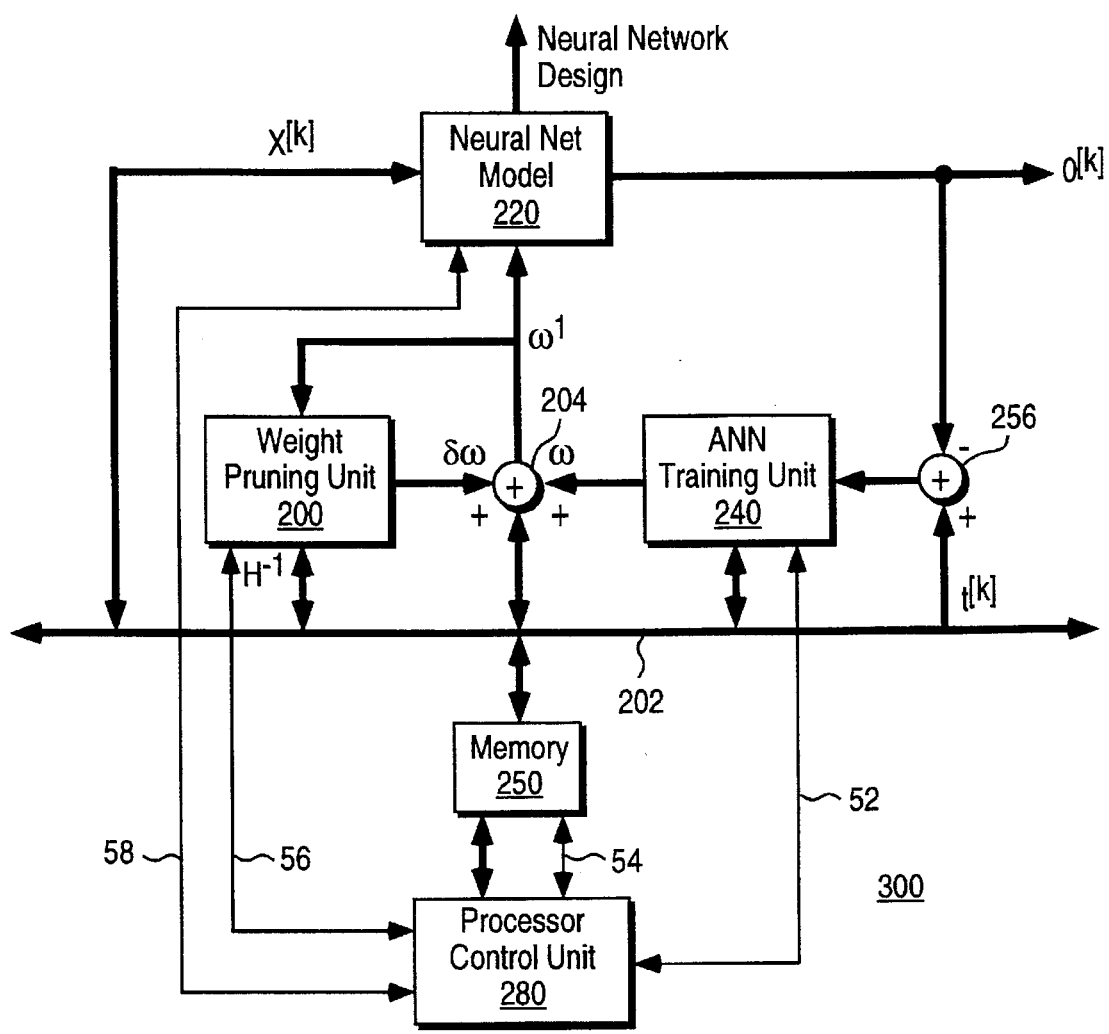
FIG. 8 is a functional block diagram of a neural network pruning design system.

FIG. 8 is a functional block diagram of a minimum connection neural network design apparatus 300 for use in the design process of neural network manufacturing. Its purpose is to determine a minimum set of interconnecting weights under the constraint of a given error budget. The error budget is expressed as an objective function which most commonly takes on the form of a minimum means square error between the actual output and the desired (exemption) output. The output from apparatus 300 is a design list of weights which are keyed to the topology of the neural network. All neural cells making up the neural network have prescribed activation functions (f(net)) that together with topology permit the calculation of the inverse Hessian, $H^{-1}$, the saliency, L, and the weight adjustment vector, $\delta w$.

The apparatus comprises a processor and control unit 280, a read/write memory 250, a memory data bus 202, an artificial neural network training unit 240, an error differencing network 256, a weight pruning unit 200, a weight adjustment adder unit 204, and a neural net model unit 220.

Processor and control unit 280 provides auxiliary numerical processing and overall control of the various elements of the apparatus, as indicated by control lines 52, 54, 56, and 58. (All data buses are indicated by bold interconnecting lines). Processor-control unit 280 data input/output interfaces with memory 250. Memory 250 data interface to processing units 200, 204, 240, 256, and 220 is via memory data bus 202.

In one embodiment, training unit 240 is a conventional gradient descent training unit using the well known back-propagation algorithm. In the training mode, training unit 240 and neural net model 220 are initialized from memory 250 via bus 202 providing initial weights, topological, and network circuit characteristics (activation functions). Training input vectors, $x^{[k]}$, are provided from memory 250 via bus 202 together with their exemplar responses, $t^{[k]}$. Neural net model 220 simulates the network response to the input vector, $x^{[k]}$, providing an output $0^{[k]}$ which is compared to $t^{[k]}$ by differencing unit 256 which forms at its output an error vector $t^{[k]}$–$0^{[k]}$ for each input/output exemplar pairs ($x^{[k]}$, $0^{[k]}$). Training unit 240 produces a new weight vector w, which is supplied via adder 204 to network model unit 220. (In the training mode, the output, δw, of pruning unit 200 is zero, thereby allowing the w to pass on through unmodified.) This updates the network model in unit 220 and iteratively converges the model to a minimum error operation point defined by the weights space. Once training is completed, the pruning process begins.

The pruning of weights is accomplished by pruning unit 200 operating cooperatively with training unit 240, adder 204, memory 250 and processor control unit 280 in accordance with the processes outlined in FIGS. 5 and 6. Pruning unit calculates $H^{-1}$ using the latest topological and weight vector information provided by training unit 240 or if stored after training from memory 250. The selected pruning operation, $w_q$, based on passing the error constraint, $E_{max}$, is used to compute a weight vector correction, δw, which may include the deletion of ineffective weights as previously discussed (steps 520, 522, of FIG. 6). The correction, δw, is added to the vector w by adder 24 to obtain the updated weight vector w which is again processed by processing unit 200 temporarily stored in memory 250.

If the error budget, $E_{max}$, is exceeded by a candidate pruning operation, the previous weight set, w', is preserved in memory 250. If retraining is deemed to be unprofitable, by actual trial or by a prior established criterion, the process ends and the updated neural network model in net model unit 20 has the necessary topology and weight value listings specifying the design may be made available to the manufacturing process steps that follow.

If retraining the remaining weights is required, the updated weight vector, w', has been made available after each pruning operation to the neural net model unit 220, or can be made available from memory 250 to model 220 and training unit 240.

Note that neural net model unit 220 may be either a real or virtual network model. If it is a virtual network, a software network simulator is used. Such simulators are used extensively in the practice of the neural network art.

In the foregoing specification, the invention has been described with reference to specific embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

What is claimed is:

1. A method for operating a design system for designing a minimal connection neural network from a given trained neural network design by iteratively pruning, by removing synaptic weights, and by adjusting any remaining synaptic weights so that the resulting neural network design performance satisfies a prescribed error budget, the design system including a processor control unit for overall control of the design system, arithmetic processing, and for providing external input/output data ports, a data memory for storage of neural network input/output data, and neural network design data, a synaptic weight pruning unit for producing a reduced connection neural network design from a given trained neural network design, a neural network modelling unit for modelling a neural network from a set of neural network design data that includes a topological network description, a set of synaptic weights, and activation function descriptions, the method for operating the design system comprising:

(a) storing the given trained neural network design data that includes a topological network description, activation function descriptions, and synaptic weight values;

(b) storing a set of exemplar input pruning vectors and corresponding response vectors for use in the neural network pruning module;

(c) initializing the neural network modelling unit using the set of trained neural network design data;

(d) operating the neural network modelling unit using the set of exemplar input pruning vectors as input data and storing each response vector in data memory;

(e) initializing the neural network pruning unit with initializing data that includes the stored trained neural network design data together with the set of exemplar pruning response vectors and the corresponding response vectors from step (d);

(f) operating the synaptic weight pruning unit for producing an iterated set of pruned neural network design data, the operating step including (i) computing a Hessian matrix of the trained neural network using the initializing data from step (d), (ii) computing an inverse Hessian matrix of the Hessian matrix of step (f)(i), (iii) computing a saliency value of each synaptic weight using the inverse Hessian matrix and the stored trained synaptic weights, (iv) selecting a synaptic weight with the smallest salient value as a selected pruning candidate weight, (v) computing a total error value that would result from pruning the selected pruning candidate weight, (vi) comparing the total error value with a specified error budget value and proceeding to step (g) if the total error value is less, otherwise terminating the method because the given trained neural network design is the minimal connection neural network design;

(g) operating the synaptic weight pruning unit for pruning and post pruning synaptic weight correction by (i) pruning the candidate weight by removing the candidate weight from the given trained neural network design data, (ii) modifying the topological network description by eliminating the pruning candidate weight branch, (iii) computing a weight correction vector, with one vector element for each remaining weight of the given trained neural network design data, that minimizes the total error value caused by pruning the pruning candidate weight, and (iv) adjusting the synaptic weights by applying the weight correction vector elements to the corresponding synaptic weights; and (h) performing another iteration by returning to step (c) and using the modified topological description and the adjusted synaptic weights of step (g) as the given trained neural network design data topological description and synaptic weights.

2. The method of claim 1 wherein step (f)(ii) computing the inverse of the Hessian matrix is an iterative process, wherein the (m+1)$^{th}$ estimate of the inverse of the Hessian matrix, H$^{-1}$, is computed in accordance with $$H_{m+1}^{-1} = H_m^{-1} - \frac{H_m^{-1} \cdot X^{[m+1]} \cdot X^{[m+1]T} \cdot H_m^{-1}}{P + X^{[m+1]T} \cdot H_m^{-1} \cdot X^{[m+1]}},$$

where: $H_0^{-1} = [a^{-1}1.]\alpha^{-1}1$, $\alpha$ is a small constant ($10^{-8} < \alpha < 10^{-4}$); I is an identity matrix; $X^{[k]}$ is a partial derivative vector calculated from the trained neural network to the k$^{th}$ input exemplar pruning vector, f(net$^{[k]}$), and $$X^{[k]} = [X_v^{[k]} \ X_u^{[k]}]^T,$$

$$X_v^{[k]} = \begin{bmatrix} f'(net^{[k]})_1 \cdot O_1^{[k]} \\ f'(net^{[k]})_2 \cdot O_2^{[k]} \\ \vdots \\ f'(net^{[k]})_{n_j} \cdot O_{n_j}^{[k]} \end{bmatrix},$$

$$X_u^{[k]} = \begin{bmatrix} f'(net^{[k]})_1 \cdot f'(net_1^{[k]})_1 \cdot v_1^{[k]} \cdot O_1^{[k]} \\ f'(net^{[k]})_1 \cdot f'(net_1^{[k]})_1 \cdot v_1^{[k]} \cdot O_2^{[k]} \\ \vdots \\ f'(net^{[k]})_1 \cdot f'(net_1^{[k]})_{n_j} \cdot v_1^{[k]} \cdot O_{n_i}^{[k]} \\ \vdots \\ f'(net^{[k]})_{n_j} \cdot f'(net_{n_j}^{[k]})_1 \cdot v_{n_j}^{[k]} \cdot O_1^{[k]} \\ f'(net^{[k]})_{n_j} \cdot f'(net_{n_j}^{[k]})_2 \cdot v_{n_j}^{[k]} \cdot O_2^{[k]} \\ \vdots \\ f'(net^{[k]})_{n_j} \cdot f'(net_{n_j}^{[k]})_{n_i} \cdot v_{n_j}^{[k]} \cdot O_{n_i}^{[k]} \end{bmatrix},$$

f'(net$^{[k]}$)$_q$ is the partial derivative of the activation function, f(net), with respect to the weight $v_q$ connecting the q$^{th}$ hidden layer output, $O_q^{[k]}$, in response to the k$^{th}$ pruning vector, evaluated at net=net$^{[k]}$, f'(net$_q^{[k]}$)$_m$ is the activation function, f(·), partial derivative with respect to m$^{th}$ weight connecting the input layer to the q$^{th}$ hidden layer, evaluation at net=net$_q$, the input value to the q$^{th}$ hidden layer activation function; P is the total number of exemplar pruning vectors, $1 \leq k \leq P$; and T is a transpose operator.

3. The method of claim 1 wherein the untrained multilayer neural network includes an input layer of $n_i$ input terminals, indexed $1 \leq i \leq n_i$, a hidden layer of $n_j$ neurons, indexed $1 \leq j \leq n_j$, each hidden layer neuron having a set of synaptic weights, $\{u_{ji}\}$, where synaptic weight $u_{ji}$ connects the j$^{th}$ hidden layer neuron to the i$^{th}$ input layer terminal, and an output layer of no neurons, indexed $1 \leq b \leq n_0$, each output layer neuron with a set of synaptic weights, $\{v_{bj}\}$, where synaptic weight $v_{bj}$ connects the j$^{th}$ hidden layer neuron output to the b$^{th}$ output layer neuron, each hidden layer and output layer neuron have an activation function, f(·), for operating on a sum of synaptic weighted input signals, net, associated with each neuron for producing a neuron output signal, f(net), step (f)(i) for computing the Hessian matrix comprising:

(a'') forming a matrix of partial derivative vectors, $\{X^{[b,k]}\}$, one partial derivative vector for each output layer neuron observed response, f(net$^{[k]}$)$_b$, where $$\begin{bmatrix} X^{[1,k]} \\ X^{[2,k]} \\ \vdots \\ X^{[n_0,k]} \end{bmatrix} = \begin{bmatrix} X_v^{[1,k]T} & X_u^{[1,k]T} \\ X_v^{[2,k]T} & X_u^{[2,k]T} \\ \vdots & \vdots \\ X_v^{[n_0,k]T} & X_u^{[n_0,k]T} \end{bmatrix},$$

$$X_v^{[b,k]} = \begin{bmatrix} f'(net^{[k]})_{1,b} \cdot O_{1,b}^{[k]} \\ f'(net^{[k]})_{2,b} \cdot O_{2,b}^{[k]} \\ \vdots \\ f'(net^{[k]})_{n_j,b} \cdot O_{n_j,b}^{[k]} \end{bmatrix},$$

$$X_u^{[b,k]} = \begin{bmatrix} f'(net^{[k]})_{1,b} \cdot f'(net_1^{[k]})_1 \cdot v_{1,b}^{[k]} \cdot O_{1,b}^{[k]} \\ f'(net^{[k]})_{1,b} \cdot f'(net_1^{[k]})_1 \cdot v_{1,b}^{[k]} \cdot O_{2,b}^{[k]} \\ \vdots \\ f'(net^{[k]})_{1,b} \cdot f'(net_1^{[k]})_1 \cdot v_{1,b}^{[k]} \cdot O_{n_i,b}^{[k]} \\ \vdots \\ f'(net^{[k]})_{n_j,b} \cdot f'(net_{n_j}^{[k]})_{n_i} \cdot v_{n_j,b}^{[k]} \cdot O_{1,b}^{[k]} \\ f'(net^{[k]})_{n_j,b} \cdot f'(net_{n_j}^{[k]})_{n_i} \cdot v_{n_j,b}^{[k]} \cdot O_{2,b}^{[k]} \\ \vdots \\ f'(net^{[k]})_{n_j,b} \cdot f'(net_{n_j}^{[k]})_{n_i} \cdot v_{n_j,b}^{[k]} \cdot O_{n_j,b}^{[k]} \end{bmatrix},$$

T is a transpose operator, k is the input exemplar pruning vector index, f'(net$^{[k]}$)$_j$ is the partial derivative of the activation function f(net) with respect to the synaptic weight $v_j$, evaluated at net=net$^{[k]}$, where net$^{[k]}$ is the value of net in response to the k$^{th}$ input exemplar pruning vector, $O_j^{[k]}$ is the j$^{th}$ hidden layer neuron output in response to the k$^{th}$ input exemplar pruning vector, f'(net$_j^{[k]}$)$_i$ is the partial derivative of the activation function with respect to $u_{ji}$ evaluated at net=net$_j^{[k]}$, the sum of all synaptic weighted input values to the j$^{th}$ hidden layer neuron activation function in response to the k$^{th}$ input exemplar pruning vector; and (b'') iteratively computing Hessian matrix estimates using the following expressions:

$$H_{b+1,k} = H_{b,k} + 1/P X^{[b+1,k]} \cdot X^{[b+1,k]T},$$

$$H_{1,k+1} = H_{n_0,k} + 1/P X^{[1,k+1]} \cdot X^{[1,k+1]T},$$

$$H_{0,k} = \alpha I,$$

$H_{n_0,P}$ is the P$^{th}$ estimate where P is the number of input exemplar pruning vectors, $\alpha$ is a small constant ($10^{-8} < \alpha < 10^{-4}$), and 1 is an identity matrix.

4. The method of claim 3 wherein step (f)(ii) of computing the inverse of the Hessian matrix is an iterative process in accordance with the following expressions:

$$H_{b+1,k}^{-1} = H_{b,k}^{-1} + \frac{H_{b,k}^{-1} \cdot X^{[b+1,k]} \cdot X^{[b+1,k]^T} \cdot H_{b,k}^{-1}}{P + X^{[b+1,k]^T} \cdot H_{b,k}^{-1} \cdot X^{[b+1,k]}},$$

$$H_{l,k+1}^{-1} = H_{l_0,k}^{-1} + \frac{H_{l_0,k}^{-1} \cdot X^{[1,k+1]} \cdot X^{[1,k+1]^T} \cdot H_{l_0,k}^{-1}}{P + X^{[1,k+1]^T} \cdot H_{l_0,k}^{-1} \cdot X^{[1,k+1]}},$$

and $$H_{0,k}^{-1} = \alpha^{-1} I.$$

5. The method of claim 1 further comprising the following steps that are executed by the synaptic pruning module prior to terminating the method of claim 17:
   (a''') identifying a set of inoperative neural cells of the trained multilayer neural network that have all of their outputs connected to pruned synaptic weights; and
   (b''') pruning the set of inoperative neural cells and their associated synaptic weights for further reducing the complexity of the trained multilayer neural network.

6. The method of claim 1 wherein the selecting step (f)(iv) is for selecting a single pruning operation candidate weight.

7. The method of claim 1 wherein the selecting step (f)(iv) is for selecting more than one low saliency pruning operation candidate weights.

8. The method of claim 1 wherein step (k)(iv) is for selecting at least one complete set of synaptic weights belonging to a common neuron.

9. The method of claim 1 wherein the synaptic weight pruning unit and the neural network modelling unit are programs operating in the processor control unit.

10. A method for operating a design system for designing a minimal connection neural network from a given untrained neural network design by training the untrained network using a set of exemplar input training vectors and a set of exemplar response vectors, then operating on the resulting trained neural network design by iteratively pruning, by removing synaptic weights, and by adjusting any remaining synaptic weights so that the resulting neural network design performance satisfies a prescribed error budget, the design system including
   a control unit for overall control of the design system and for providing external input/output data ports,
   a data memory for storage of neural network input/output data, and neural network design data,
   a neural network training unit for training of an untrained neural network and for producing a trained neural network design by using a set of exemplar training input vectors and corresponding exemplar response vectors,
   a synaptic weight pruning unit for producing a reduced connection neural cell design from a given trained neural network design,
   a neural network modelling unit for modelling a neural network from a set of neural network design data that includes a topological network description, a set of synaptic weights, and activation function descriptions,
the method for operating the design system comprising:
   (a) storing the untrained neural network design that includes a topological network description, activation function descriptions, and synaptic weight values,
   (b) storing a set of exemplar input and output training vectors;
   (c) initializing the neural network modelling unit with a set of untrained neural network design data that includes a topological network description, a set of synaptic weights, and activation function descriptions,
   (d) operating the neural network training unit for controlling the neural network modelling module for generating a response to a set of exemplar input training vectors, comparing each response vector to a corresponding exemplar response vector, and adjusting the untrained neural network set of synaptic weights in accordance with a known training procedure, for generating a description of a trained neural network design data,
   (e) storing the trained neural network design data that includes a topological network description, activation function descriptions, and synaptic weight values;
   (f) storing of a set of exemplar input pruning vectors and corresponding response vectors for use in the neural network pruning unit;
   (g) initializing the neural network modelling unit using the trained neural network design data;
   (h) operating the neural network modelling unit using the set of exemplar input pruning vectors as input data and storing each response vector in data memory;
   (j) initializing the neural network pruning unit using the stored trained neural network design data together with the set of exemplar pruning response vectors and the corresponding response vectors from step (h);
   (k) operating the neural network pruning unit for producing an iterated set of pruned neural network design data, the operating step including
      (i) computing a Hessian matrix of the trained neural network using the data from step (h),
      (ii) computing an inverse Hessian matrix of the Hessian matrix of step (h)(i),
      (iii) computing a saliency value of each synaptic weight using the inverse Hessian matrix and the stored trained synaptic weights,
      (iv) selecting a synaptic weight with the smallest salient value as a selected pruning candidate weight,
      (v) computing a total error value that would result from pruning the selected pruning candidate weight,
      (vi) comparing the total error value with a specified error budget value and proceeding to step (I) if the total error value is less, otherwise terminating the method;
   (l) operating the synaptic weight pruning module for pruning and post pruning synaptic weight correction by
      (i) pruning the candidate weight by removing the candidate weight from the trained neural network design data,
      (ii) modifying the topological network description by eliminating the pruning candidate weight branch,
      (iii) computing a weight correction vector, with one vector element for each remaining weight of the trained neural network design data, that minimizes the total error value caused by pruning the pruning candidate weight, and
      (iv) adjusting the synaptic weights by applying the weight correction vector elements to the corresponding synaptic weights; and
   (m) performing another iteration by returning to step (g) and using the modified topological description and the adjusted synaptic weights of step (I) as the trained neural network design data topological description and synaptic weights.

11. The method of claim 10 wherein the untrained multilayer neural network includes an input layer of $n_i$ input terminals, indexed $1 \leq i \leq n_i$, a hidden layer of $n_j$ neurons, index $1 \leq j \leq n_j$, each hidden layer neuron having a set of synaptic weights, $\{u_{ji}\}$, where synaptic weight $u_{ji}$ connects the $j^{th}$ hidden layer neuron to the $i^{th}$ input layer terminal, and an output layer neuron with a set of synaptic weights, $\{v_j\}$, where synaptic weight $v_j$ connects the output of the $j^{th}$ hidden layer neuron, each hidden layer neuron and the output layer neuron having an activation function $f(\cdot)$ for operating on a sum of synaptic weighted input signals, net, associated with each neuron for producing a neuron output signal $f(net)$, the step of computing the Hessian matrix comprising:

(a') forming a $k^{th}$ partial derivative vector, $X^{[k]}$, from the observed output layer response $f(net^{[k]})$ where $net^{[k]}$ is the value of net for the output layer neuron is response to a $k^{th}$ input exemplar pruning vector, where $$X^{[k]} = [X_v^{[k]} \; X_u^{[k]}]^T,$$

$$X_v^{[k]} = \begin{bmatrix} f'(net^{[k]})_1 \cdot O_1^{[k]} \\ f'(net^{[k]})_2 \cdot O_2^{[k]} \\ \vdots \\ f'(net^{[k]})_{n_j} \cdot O_{n_j}^{[k]} \end{bmatrix},$$

$$X_u^{[k]} = \begin{bmatrix} f'(net^{[k]})_1 \cdot f'(net_1^{[k]})_1 \cdot v_1^{[k]} \cdot O_1^{[k]} \\ f'(net^{[k]})_1 \cdot f'(net_1^{[k]})_2 \cdot v_1^{[k]} \cdot O_2^{[k]} \\ \vdots \\ f'(net^{[k]})_1 \cdot f'(net_1^{[k]})_{n_j} \cdot v_1^{[k]} \cdot O_{n_i}^{[k]} \\ \vdots \\ f'(net^{[k]})_{n_j} \cdot f'(net_{n_j}^{[k]})_1 \cdot v_{n_j}^{[k]} \cdot O_1^{[k]} \\ f'(net^{[k]})_{n_j} \cdot f'(net_{n_j}^{[k]})_2 \cdot v_{n_j} \cdot O_2^{[k]} \\ \vdots \\ f'(net^{[k]})_{n_j} \cdot f'(net_{n_j}^{[k]})_{n_i} \cdot v_{n_j} \cdot O_{n_i}^{[k]} \end{bmatrix},$$

$f'(net^{[k]})_b$ is the partial derivative of $f(net^{[k]})_b$, the output layer $b^{th}$ neuron response to the $k^{th}$ input exemplar pruning vector, with respect to the weight $v_{bj}$ that connects the output of the $j^{th}$ hidden layer neuron to the $b^{th}$ output layer neuron, evaluated at $net=net^{[k]}$, and $1 \leq b \leq n_j$, T is a transpose operator, $o_{j,b}^{[k]}$ is the output of the hidden layer $j^{th}$ neuron in response to the $k^{th}$ input exemplar pruning vector, $f'(net_j^{[k]})_i$ is the partial derivative of the activation function with respect to $u_{ji}$ evaluated at $net=net^{[k]}$, the sum of all synaptic weighted input values to the $j^{th}$ hidden layer neuron activation function in response to the $k^{th}$ input exemplar pruning vector; and (b') iteratively computing a Hessian matrix estimate, $H_{m+1}$, from (m+1) successive partial derivative vectors in accordance with $$H_{m+1} = H_m + \frac{1}{m+1} X^{[m+1]} \cdot X^{[m+1]T}$$

where $H_b = \alpha 1$, 1 is an identity matrix, $\alpha$ is a small constant ($10^{-8} < \alpha < 10^{-4}$), until m+1=P so that Hp is a final Hessian matrix obtained by using P input exemplar pruning vectors.

12. The method of claim 10 wherein the neural network training unit, the synaptic weight pruning unit, and the neural network modelling unit are programs operating in the processor control unit.

* * * * *